US009101473B2

(12) United States Patent
Sweeney et al.

(10) Patent No.: US 9,101,473 B2
(45) Date of Patent: Aug. 11, 2015

(54) VENOUS VALVE REPAIR PROSTHESIS FOR TREATMENT OF CHRONIC VENOUS INSUFFICIENCY

(71) Applicant: Medtronic Vascular, Inc., Santa Rosa, CA (US)

(72) Inventors: Fiachra Sweeney, Parkavera (IE); Michael Cummins, Roscam (IE); Kent Martin, Bisbane (AU); Stefanie Ahlrichs, Dresden (DE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 13/788,561

(22) Filed: Mar. 7, 2013

(65) Prior Publication Data
US 2014/0257463 A1  Sep. 11, 2014

(51) Int. Cl.
*A61F 2/24* (2006.01)
*A61F 2/88* (2006.01)

(52) U.S. Cl.
CPC .............. *A61F 2/2475* (2013.01); *A61F 2/2418* (2013.01); *A61F 2/88* (2013.01); *A61F 2230/0091* (2013.01)

(58) Field of Classification Search
CPC ............... A61F 2/06; A61F 2/86; A61F 2/88; A61F 2/2475; A61F 2/2418; A61F 2/24; A61F 2230/0091; A61F 2/82
USPC ........... 623/1.11, 1.12, 1.15, 1.22, 1.24, 2.11, 623/1.14, 1.2, 1.26, 2.14, 2.17, 2.18, 2.38; 267/166
See application file for complete search history.

(56) References Cited

U.S. PATENT DOCUMENTS

| 4,655,771 | A | * | 4/1987 | Wallsten ...................... 623/1.22 |
| 5,607,445 | A | * | 3/1997 | Summers ...................... 623/1.22 |
| 5,772,668 | A | * | 6/1998 | Summers et al. ............. 623/1.11 |
| 7,416,557 | B2 | | 8/2008 | Drasler et al. |
| 2007/0112423 | A1 | | 5/2007 | Chu |
| 2010/0106162 | A1 | * | 4/2010 | Jaeger et al. .................. 606/108 |
| 2011/0218619 | A1 | * | 9/2011 | Benichou et al. ............ 623/2.11 |

* cited by examiner

*Primary Examiner* — David Isabella
*Assistant Examiner* — Rokhaya Diop

(57) ABSTRACT

Endovascular prostheses are disclosed that are configured to repair a native venous valve having improper or non-existent valve leaflet coaptation caused by vessel weakness and/or distention. The prostheses are configured to be implanted in the venous system immediately downstream of the malfunctioning valve and act as repair devices to restore proper function to the venous valve by reconfiguring and supporting the valve leaflets and thereby improving their coaptation.

11 Claims, 9 Drawing Sheets

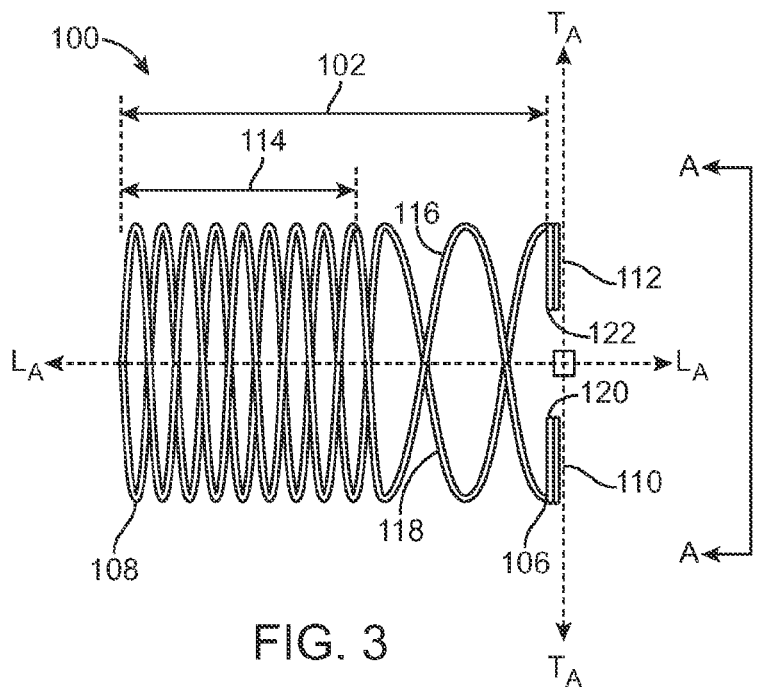
FIG. 3
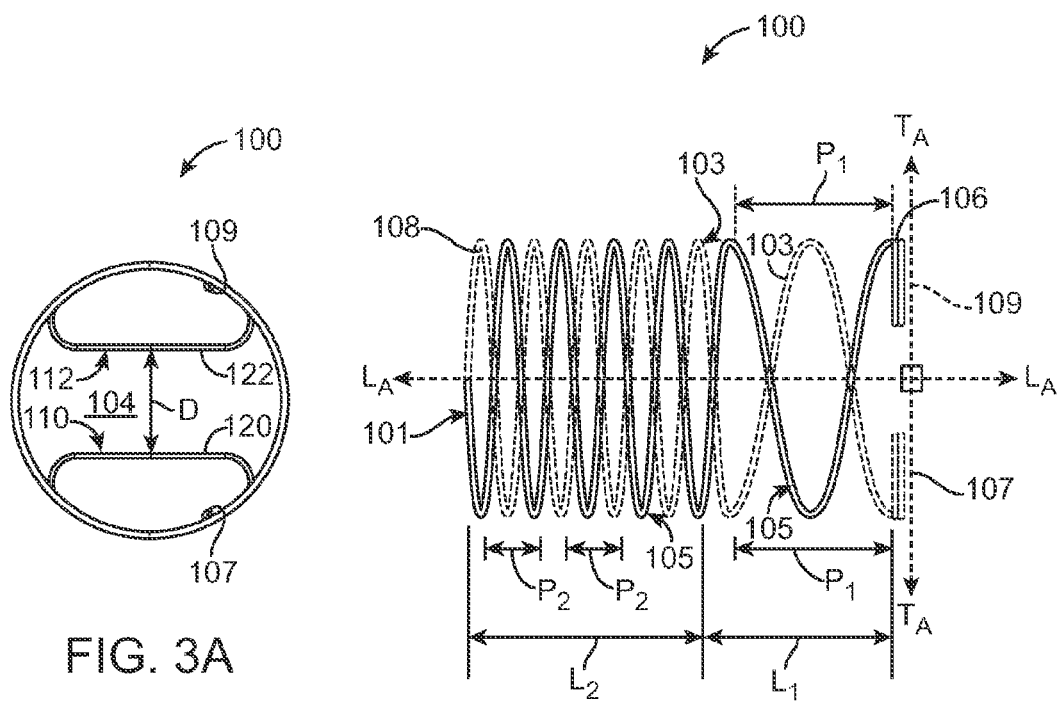
FIG. 3A
FIG. 3B

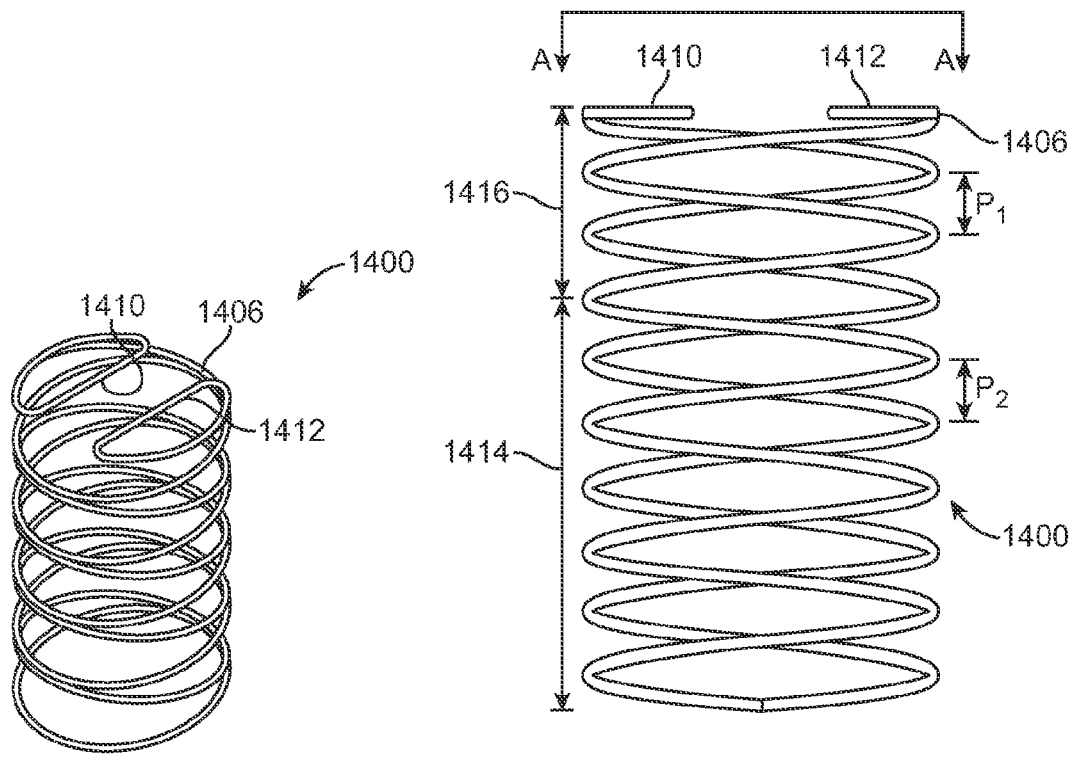
FIG. 14
FIG. 15
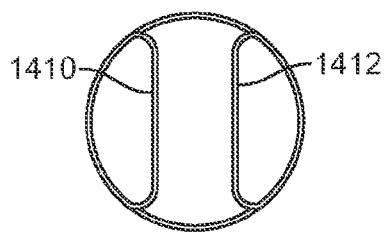
FIG. 15A

VENOUS VALVE REPAIR PROSTHESIS FOR TREATMENT OF CHRONIC VENOUS INSUFFICIENCY

FIELD OF THE INVENTION

The invention relates to endovascular prostheses for treatment of chronic venous insufficiency and more particularly to venous valve repair prostheses for restoring apposition to valve leaflets of a malfunctioning venous valve.

BACKGROUND OF THE INVENTION

Venous valves are self-closing, one-way valves found within native veins and are used to assist in returning blood back to the heart in an antegrade blood flow direction from all parts of the body. The venous system of the leg for example includes the deep venous system and the superficial venous system, both of which are provided with venous valves that are intended to prevent retrograde flow, which can lead to blood pooling or stasis in the leg. Incompetent valves can also lead to reflux of blood from the deep venous system to the superficial venous system and the formation of varicose veins. Superficial veins which include the greater and lesser saphenous veins have perforating branches in the femoral and popliteal regions of the leg that direct blood flow toward the deep venous system and generally have a venous valve located near the junction with the deep venous system. Deep veins of the leg include the anterior and posterior tibial veins, popliteal veins, and femoral veins. Deep veins are surrounded in part by muscular tissues that assist in generating flow by muscle contraction during normal walking or exercising.

Blood pressure in the veins of the lower leg of a healthy person may range from 0 mm Hg to over 200 mm Hg, depending on factors such as the activity of the body (i.e., stationary or exercising), the position of the body (i.e., supine or standing), and the location of the vein (i.e., ankle or thigh). For example, venous pressure may be approximately 80-90 mm Hg while standing and may be reduced to 60-70 mm Hg during exercise. Despite exposure to such pressures, the valves of the leg are very flexible and can close with a pressure differential of less than one mm Hg.

Veins typically in the leg can become distended from prolonged exposure to excessive blood pressure and due to weaknesses found in the vessel wall. Distension of veins can cause the natural valves therein to become incompetent leading to retrograde blood flow in the veins. Such veins no longer function to help pump or direct the blood back to the heart during normal walking or use of the leg muscles. As a result, blood tends to pool in the lower leg and can lead to leg swelling and the formation of deep venous thrombosis and phlebitis. The formation of thrombus in the veins can further impair venous valvular function by causing valvular adherence to the venous wall with possible irreversible loss of venous function. Continued exposure of the venous system to blood pooling and swelling of the surrounding tissue can lead to post phlebitic syndrome with a propensity for open sores, infection, and may lead to limb amputation.

Chronic venous insufficiency (CVI) occurs in patients that have deep and superficial venous valves of their lower extremities (distal to their pelvis) that have failed or become incompetent due to the aforementioned vessel weakness as well as, for e.g., valve prolapse, congenital valvular abnormalities, such as missing valves, and/or vascular disease that results in valve damage. As a result, such patients may suffer from varicose veins, swelling and pain of the lower extremities, edema, hyper pigmentation, lipodermatosclerosis, and/or deep vein thrombosis (DVT). Such patients are at increased risk for development of soft tissue necrosis, ulcerations, pulmonary embolism, stroke, heart attack, and amputations.

Repair and replacement of venous valves presents a formidable challenge due to the low blood flow rate found in native veins, the very thin and distensible wall structure of the venous wall and the venous valve, and the ease and frequency with which venous blood flow can be impeded or totally blocked for a period of time. Surgical reconstruction techniques used to address venous valve incompetence include venous valve bypass using a segment of vein with a competent valve, venous transposition to bypass venous blood flow through a neighboring competent valve, and valvuloplasty to repair the valve cusps. These surgical approaches may involve placement of synthetic, allograft and/or xenograft prostheses inside of or around the vein. However, such prostheses have not been devoid of problems, such as thrombus formation and valve failure due to the implanted prostheses causing non-physiologic flow conditions and/or excessive dilation of the vessels with a subsequent decrease in blood flow rates.

Percutaneous endoluminal methods for treatment of venous insufficiency are being studied, some of which include placement of synthetic, allograft and/or xenograft valve prosthesis that suffer from similar problems as the surgically implanted ones discussed above. In light thereof, there is still a need in the art for an improved device that may be percutaneously placed within a vein having an existing insufficient, malfunctioning venous valve to re-establish apposition between the valve leaflets to thereby restore proper flow through the vein segment.

BRIEF SUMMARY OF THE INVENTION

Embodiments hereof are directed to an implant or prosthesis configured to repair a venous valve that has improper or non-existent valve leaflet coaptation caused by vessel weakness and/or distention. The implant is configured to be implanted in the venous system immediately downstream, i.e., closer to the heart in the direction of blood flow, of the malfunctioning valve and acts as a repair device to restore proper function to the venous valve by reconfiguring and supporting the valve leaflets to thereby improve their coaptation.

In an embodiment, the prosthesis has a tubular body that defines a blood flow lumen along a longitudinal axis of the prosthesis, wherein the tubular body includes an anchor portion for securing a longitudinal position of the prosthesis within the vessel, and a plurality of valve apposition portions longitudinally separated from the anchor portion by respective connector portions. The valve apposition portions are disposed toward each other relative to the longitudinal axis of the prosthesis from respective connector portions and are spaced apart a distance for receiving the native valve leaflets therebetween.

In an embodiment, a wire of a superelastic or resilient material is formed into a first helix from a distal end to a proximal end of the prosthesis and a second overlaying helix from the proximal end to the distal end of the prosthesis to define the tubular body of the prosthesis. Free ends of the wire at a distal end of the prosthesis define respective valve apposition portions with distal lengths of the first and second helix forming respective connector portions of the prosthesis and proximal lengths of the first and second helix forming an anchor portion of the prosthesis.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3 is a side view of a venous valve repair prosthesis in accordance with an embodiment hereof.

FIG. 3A is an end view of the prosthesis of FIG. 3 taken in the direction of line A-A thereof.

FIG. 3B is a modified side view of the prosthesis of FIG. 3 depicting first and second helix of a wire wrapped to form the prosthesis.

FIG. 14 is a perspective view of a venous valve repair prosthesis in accordance with another embodiment hereof.

FIG. 15 is a side view of the prosthesis of FIG. 14.

FIG. 15A is an end view of the prosthesis of FIG. 15 taken in the direction of line A-A thereof.

DETAILED DESCRIPTION OF THE INVENTION

Specific embodiments of the present invention are described below with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, the term "self-expanding" is used in the following description with reference to the prostheses hereof and is intended to convey that the structures are shaped or formed from a material that can be provided with a mechanical memory to return the structure from a compressed or constricted delivery configuration to an expanded deployed configuration. Non-exhaustive exemplary materials that are suitable for forming self-expanding prosthesis in accordance with embodiments hereof include stainless steel, a pseudo-elastic metal such as a nickel titanium alloy or nitinol, or a so-called super alloy, which may have a base metal of nickel, cobalt, chromium, or other metal. Mechanical memory may be imparted to a wire or other structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprolactone copolymer and poly cyclo-octine can be used separately or in conjunction with other shape memory polymers.

The following detailed description is merely exemplary in nature and is not intended to limit the invention or the application and uses of the invention. Although the description of embodiments hereof are in the context of treatment of blood vessels such as the superficial leg veins, the invention may also be used in any other body vessels and passageways where it is deemed useful. Furthermore, there is no intention to be bound by any expressed or implied theory presented in the preceding technical field, background, brief summary or the following detailed description.

Figure 1A:
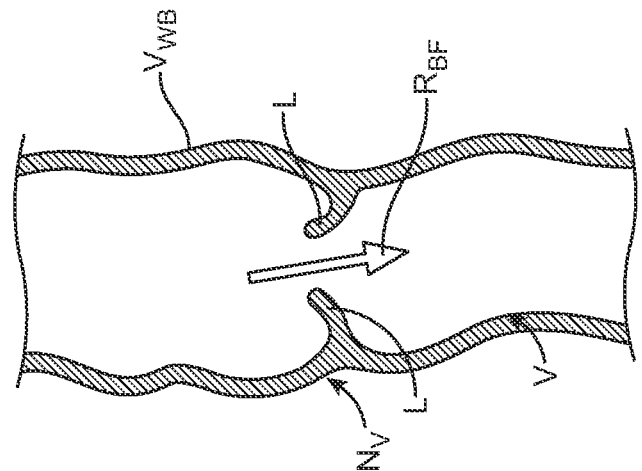
FIGS. 1A-1B are schematic representations of open and closed configurations of a healthy valve within a vein.
Figure 1B:
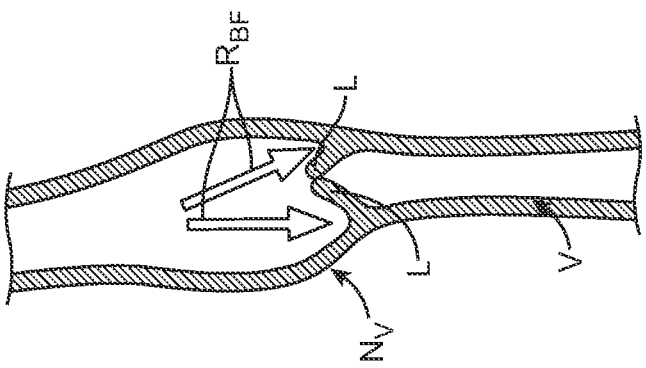

FIGS. 1A-1B are schematic representations of the function of a healthy native valve $N_V$ within a vein V. Valves within the venous system are configured in a variety of shapes that depend on anatomical location, vessel size, and function. For example, the typical shape of the venous valve in man includes two flaps, a.k.a. cusps or leaflets having free edges that sealingly meet, when closed, to form a commissure. Venous valves are typically associated with a broadened area of the vein forming a sinus pocket behind each leaflet. The natural venous valve leaflet configuration referenced herein is for clarity of function and is not limiting in the application of the referenced embodiments. Venous valve $N_V$ controls blood flow through the lumen defined by vein V via leaflets L. More particularly, venous valve $N_V$ opens to allow antegrade blood flow $A_{BF}$ through leaflets L and toward the heart as shown in FIG. 1A. Venous valve $N_V$ closes to prevent backflow or retrograde blood flow $R_{BF}$ through leaflets L as shown in FIG. 1B.

Figure 2:
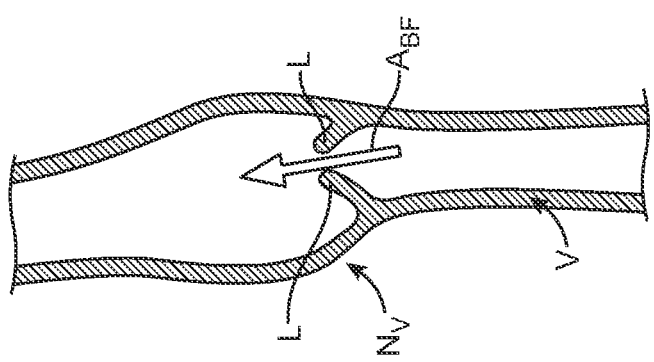
FIG. 2 is a schematic representation of retrograde blood flow through an incompetent or malfunctioning valve within a vein.

FIG. 2 is a schematic representation of retrograde blood flow through an incompetent venous valve due to vessel weakness. Backflow or retrograde blood flow $R_{BF}$ leaks through venous valve $N_V$ creating blood build-up that eventually may destroy the venous valve and cause a venous wall bulge $V_{WB}$. More specifically, the wall of vein V may expand into a pouch or bulge, such that the vessel has a knotted external appearance when the pouch is filled with blood. The distended vessel wall area may occur on the outflow or downstream side of the valve above leaflets L as shown in FIG. 2, and/or on the inflow or upstream side of the valve below leaflets L. After a venous valve segment becomes incompetent, the vessel wall dilates and fluid velocity therethrough decreases, which may lead to flow stasis and thrombus formation in the proximity of the venous valve.

FIG. 3 is a side view of a venous valve repair prosthesis 100 in a deployed or expanded configuration in accordance with an embodiment hereof with FIG. 3A being an end view of prosthesis 100 taken in the direction of line A-A of FIG. 3 and with FIG. 3B being a modified side view of prosthesis 100 that depicts first and second helix 103, 105 of a wire 101 wrapped to form prosthesis 100. In accordance with embodiments hereof, wire 101 may be a single wire or ribbon of a material noted above, or one or more joined wires or ribbons of the same or different materials noted above without departing from the scope hereof. Prosthesis 100 is a self-expanding endovascular prosthesis that is deformable or compressible into a reduced diameter delivery configuration (as shown in FIG. 5A) to be percutaneously deliverable to a treatment site within the vasculature via a delivery catheter, wherein prosthesis 100 returns to an expanded or deployed configuration as shown in FIG. 3 upon release from the delivery catheter during implantation. In an embodiment, self-expanding prosthesis 100 is formed from wire 101 of a shape memory material, such as nitinol or one of the other materials noted above, that has been wrapped around a suitable mandrel and heat treated to define a tubular body 102 having a blood flow lumen 104 extending along a longitudinal axis $L_A$ thereof. Generally as depicted in FIG. 3B, wire 101 is wrapped in a first direction such that a first helix 103 (shown as a dashed line) is formed to extend from a first or distal end 106 of prosthesis 100 to a second or proximal end 108 of prosthesis 100 and is then wrapped back over itself in a second direction opposite of the first direction such that a second helix 105 (shown as a solid line) is formed to extend from the second or proximal end 108 of prosthesis 100 to the first or distal end 106 of prosthesis 100 to thereby define tubular body 102. As such, respective windings of the second helix 105 are wound on top of the windings of the first helix 103 and the first and second helix 103, 105 may be considered to be wound in opposite directions, such that one helix is right-handed and the other is left-handed. With wire 101 wrapped or wound to form tubular body 102 as noted above, first and second ends 107, 109 of wire 101, which are also referred to herein as the free ends 107, 109 of wire 101, are each disposed at distal end 106 of prosthesis 100 and are each shaped into a closed loop to define a pair of first and second valve apposition portions 110, 112 of prosthesis 100, as discussed in detail below.

Tubular body 102 of wire 101 is formed to include an anchor portion 114, a pair of first and second connector portions 116, 118 and the pair of first and second valve apposition portions 110, 112, wherein the pair of valve apposition portions 110, 112 are longitudinally displaced from anchor portion 114 by respective connector portions 116, 118. Anchor portion 114 is configured to secure a longitudinal position of prosthesis 100 within a healthy portion of the vein downstream of the native valve to be repaired, with connector portions 116, 118 configured to extend through the weakened area of the vessel to position the valve apposition portions 110, 112 at the valve leaflets, as discussed in more detail below. First or distal lengths $L_1$ of first and second helix 103, 105 form respective connector portions 116, 118 and second or proximal lengths $L_2$ of overlaying first and second helix 103, 105 form anchor portion 114, wherein a first pitch $P_1$ between respective windings of the first and second helix 103, 105 that form respective connector portions 116, 118 is greater than a second pitch $P_2$ between respective windings of the overlaying first and second helix 103, 105 that form anchor portion 114. In the configuration shown in FIG. 3, anchor portion 114 with windings that are closer together than the windings in the connector portions 116, 118 is less flexible and provides firm support of the prosthesis within the vessel, with connector portions 116, 118 providing a more flexible attachment for first and second valve apposition portions 110, 112. In another embodiment, the density or pitch between, and/or angle of consecutive windings may be varied along the length $L_2$ of anchor portion 114 to provide additional longitudinal flexibility thereto. In another embodiment for certain applications, an inverse relationship of the pitch or distance between windings of the anchor portion versus the pitch or distance between windings of the connector portions may be desired, i.e., with the anchor portion having a greater pitch between windings than the pitch between windings of the connector portions, such that the anchor portion is made more flexible than the connector portions.

Valve apposition portions 110, 112 extend toward each other from their respective connector portions 116, 118 to be substantially transverse or at a right angle with respect to longitudinal axis $L_A$ of prosthesis 100, as depicted by transverse axis $T_A$ in FIGS. 3 and 3B. Valve apposition portions 110, 112 are aligned with each other along transverse axis $T_A$ such that respective valve contacting segments 120, 122 thereof are spaced apart a suitable distance D for receiving leaflets of a native valve therebetween when prosthesis 100 is implanted. In the embodiment of FIGS. 3, 3A and 3B, valve apposition portions 110, 112 define substantially parallel valve contacting segments 120, 122 that are configured for supporting the native valve leaflets therebetween. By substantially parallel it is meant that the valve contacting segments 120, 122 extend along the same transverse plane or parallel transverse planes of the prosthesis or one or the other may deviate therefrom by plus or minus 5 degrees. In embodiments hereof, distance D between valve contacting segments 120, 122 of valve apposition portions 110, 112 is within the range of less than 1 mm to 24 mm to be suitable for use in repairing venous valves of the superficial and deep leg veins, such as for placement within the common femoral vein. In another embodiment, distance D may be sized to be equal to substantially one third of a diameter of the vessel in which it is to be implanted.

Figure 9:
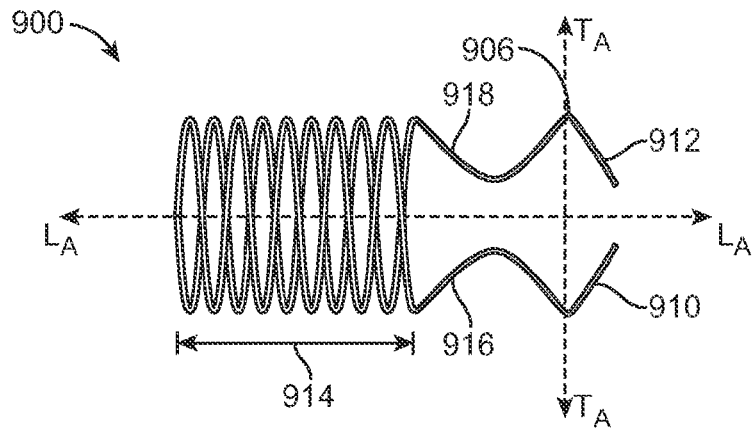
FIG. 9 is a side view of a venous valve repair prosthesis in accordance with another embodiment hereof.
Figure 10:
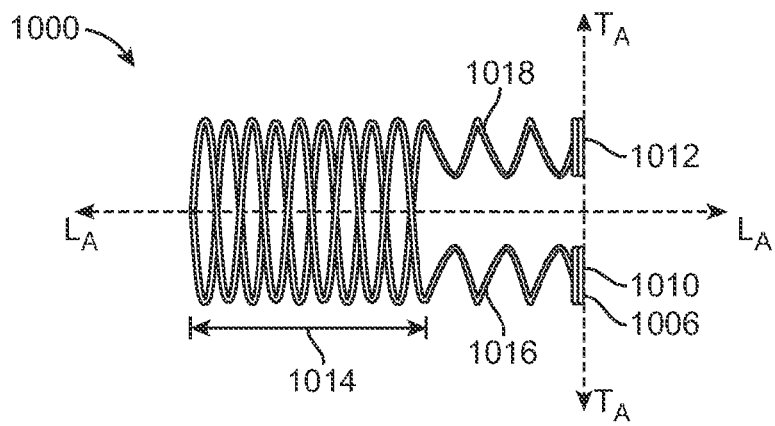
FIG. 10 is a side view of a venous valve repair prosthesis in accordance with another embodiment hereof.
Figure 11:
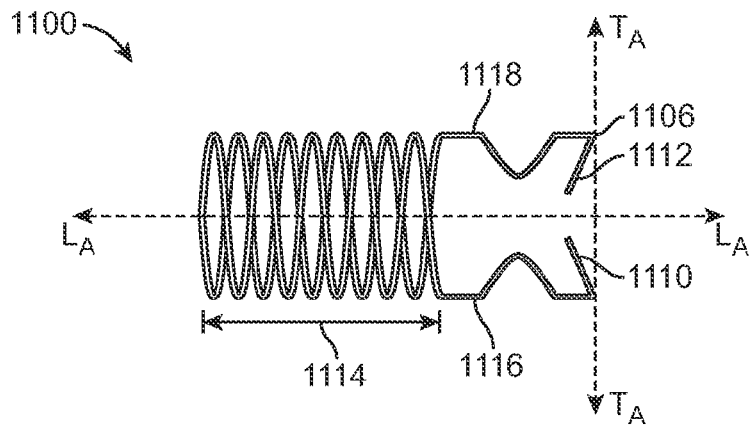
FIG. 11 is a side view of a venous valve repair prosthesis in accordance with another embodiment hereof.

FIGS. 9-11 are side views of venous valve repair prosthesis 900, 1000, 1100, respectively, in a deployed or expanded configuration that illustrate variations of connector portions and valve apposition portions in accordance with various embodiments hereof. With reference to FIG. 9, prosthesis 900 includes an anchor portion 914, first and second connector portions 916, 918 and first and second valve apposition portions 910, 912. Valve apposition portions 910, 912 are angled outward or distally of a transverse axis $T_A$ at distal end 906 of the prosthesis to be at other than a right angle with respect to longitudinal axis $L_A$ of prosthesis 900 and are longitudinally displaced from anchor portion 914 by respective connector portions 916, 918, each of has a swag or curved shape. With reference to FIG. 10, prosthesis 1000 includes an anchor portion 1014, first and second connector portions 1016, 1018 and first and second valve apposition portions 1010, 1012. Valve apposition portions 1010, 1012 extend toward each other from distal end 1006 of the prosthesis to be at right angles with respect to longitudinal axis $L_A$ of prosthesis 1000 and are longitudinally displaced from anchor portion 1014 by respective connector portions 1016, 1018, each of which has a sinusoidal or wave-like shape. With reference to FIG. 11, prosthesis 1100 includes an anchor portion 1114, first and second connector portions 1116, 1118 and first and second valve apposition portions 1110, 1112. Valve apposition portions 1110, 1112 are angled inward or proximally of a transverse axis $T_A$ at distal end 1106 of the prosthesis to be at other than a right angle with respect to longitudinal axis $L_A$ of prosthesis 1100 and are longitudinally displaced from anchor portion 1114 by respective connector portions 1116, 1118, each of which is substantially straight with a swag or inwardly curved section therein. The connector portions of prosthesis 900, 1000, 1100 are configured to be radially apposed to a wall of the vessel in the same orientation as the respective anchor portions thereof. With reference to the various angles at which valve apposition portions of prosthesis 900, 1000, 1100 may be disposed relative the longitudinal axis of the prosthesis, each orientation permits a different level of support to be provided to the valve leaflets, with the outwardly extending valve apposition portions 910, 912 of prosthesis 900 considered to provide the least support to the valve leaflets and valve apposition portions 1110, 1112 of prosthesis 1100 considered to provide the most support to the valve leaflets.

In accordance with embodiments hereof, prosthesis 900, 1000, 1100 may be formed from a single wire or one or more joined wires of a material noted above with overlaying helices as described above with reference to the embodiment of FIG. 3, or interlaying helices with windings of one helix alternately crossing over and then under windings of the other helix. In accordance with other embodiments hereof, prosthesis 900, 1000, 1100 may be formed from a plurality of wires of a material noted above having the windings aligned such that parallel right-handed or left-handed helices are formed, as described below with reference to the embodiment of FIGS. 12, 13 and 13A.

Figures 12, 13:
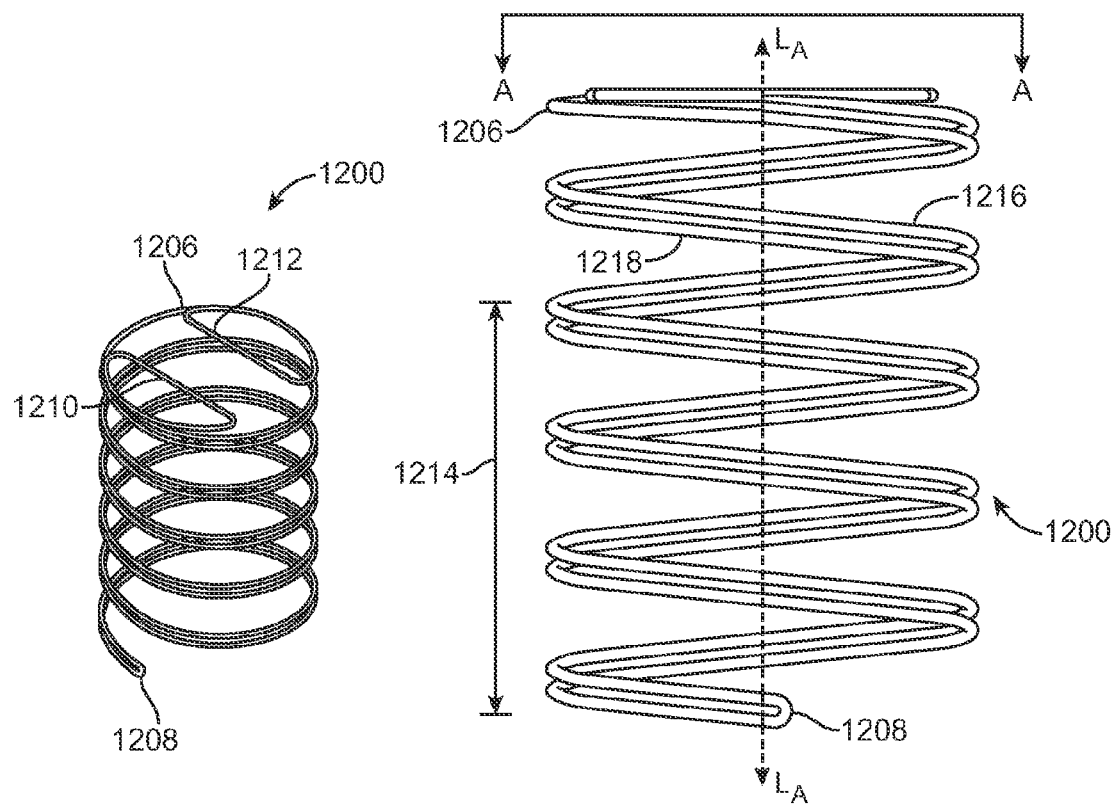
FIG. 12 is a perspective view of a venous valve repair prosthesis in accordance with another embodiment hereof.
FIG. 13 is a side view of the prosthesis of FIG. 12.
Figure 13A:
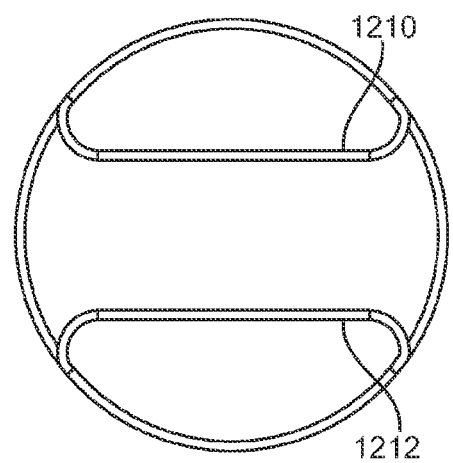
FIG. 13A is an end view of the prosthesis of FIG. 13 taken in the direction of line A-A thereof.

FIG. 12 is a perspective and FIG. 13 is a side view of a venous valve repair prosthesis 1200 in a deployed or expanded configuration in accordance with another embodiment hereof, with FIG. 13A depicting an end view of the prosthesis taken in the direction of line A-A of FIG. 13. Prosthesis 1200 includes an anchor portion 1214, first and second connector portions 1216, 1218 and first and second valve apposition portions 1210, 1212. Anchor portion 1214 is configured to secure a longitudinal position of prosthesis 1200 within a healthy portion of the vein downstream of the native valve to be repaired and may include a greater or lesser portion of prosthesis 1200 than is shown in FIG. 13, with connector portions 1216, 1218 being the remainder of prosthesis 1200 that are configured to extend through the weakened area of the vessel to position the valve apposition portions 1210, 1212 at the valve leaflets, as discussed in more detail below with reference to the embodiment of FIG. 3. Valve apposition portions 1210, 1212 extend toward each other from distal end 1206 of the prosthesis 1200 to be at right angles with respect to longitudinal axis $L_A$ of prosthesis 1200 but in alternate embodiments may be angled outward or inward as previously discussed above with reference to the embodiment of FIGS. 9 and 11 for certain applications.

In the embodiment of FIGS. 12, 13 and 13A, prosthesis 1200 is formed by winding at least two wires of a material noted above in parallel such that the windings of the subsequently formed helices are aligned with each other and therefore both run in the same direction. As shown in FIGS. 12 and 13, the dual helix that form prosthesis 1200 run in a counter-clockwise direction as viewed from a proximal end 1208 of the prosthesis such that each helix is a left-handed helix. It would be understood by one of skill in the art that the dual helix of prosthesis 1200 may run in a clockwise direction such that each helix is a right-handed helix without departing from the scope hereof. The dual windings that form anchor portion 1214 have the same pitch or distance between consecutive windings as the respective windings that form connector portions 1216, 1218. In contrast to the embodiments of FIGS. 3 and 9-11, aligned or parallel windings as shown in anchor portion 1214 may provide more longitudinal flexibility to that portion of prosthesis 1200 than the overlapping or interlaid windings of anchor portions 314, 914, 1014, 1114 as shown and described above, which may be considered as providing relatively more radial rigidity to that portion of prosthesis 100, 900, 1000, 1100, respectively. In another embodiment, the pitch between the dual windings of the anchor portion of prosthesis 1200 and the pitch between the respective windings that form the connector portions may be varied, i.e., greater or lesser with respect to each other, depending on whether more or less flexibility or radial strength is desired in one or both of those regions of the prosthesis.

FIG. 14 is a perspective and FIG. 15 is a side view of a venous valve repair prosthesis 1400 in a deployed or expanded configuration in accordance with another embodiment hereof, with FIG. 15A depicting an end view of the prosthesis taken in the direction of line A-A of FIG. 15. Prosthesis 1400 includes an anchor portion 1414, a connector portion 1416 and first and second valve apposition portions 1410, 1412. Anchor portion 1414 is configured to secure a longitudinal position of prosthesis 1400 within a healthy portion of the vein downstream of the native valve to be repaired and may include a greater or lesser portion of prosthesis 1400 than is shown in FIG. 15, with connector portion 1416 being the remainder of prosthesis 1400 that is configured to extend through the weakened area of the vessel to position the valve apposition portions 1410, 1412 at the valve leaflets, as discussed in more detail below with reference to the embodiment of FIG. 3. Valve apposition portions 1410, 1412 extend toward each other from distal end 1406 of the prosthesis 1400 to be at right angles with respect to longitudinal axis $L_A$ of prosthesis 1400 but in alternate embodiments may be angled outward or inward as previously discussed above with reference to the embodiment of FIGS. 9 and 11 for certain applications.

In the embodiment of FIGS. 14, 15 and 15A, prosthesis 1400 is formed in an expanded or deployed configuration by laser cutting a tube of a shape memory material into the pattern shown in the figures and heat setting the cut tube, as would be known to one of ordinary skill in the art. Accordingly, prosthesis 1400 would act differently as it returns to the expanded configuration from a compressed delivery configuration from the wire-formed prosthesis described above due to the solid nature of the "connections" of prosthesis 1400, as relative movement that is permitted between the overlaying or interlaying wires of the prior embodiments is eliminated. Valve apposition portions 1410, 1412 may be integral portions of the cut tube that are bent into the position shown in the figures prior to shape setting the cut tube, or may be separately formed components that are subsequently joined thereto by any suitable method known in the art. In embodiments hereof, a suitable shape memory material for such a tube includes but is not limited to nitinol. In an embodiment, a density or pitch $P_1$ of the cut pattern in connector portion 1416 may be increased relative to a density or pitch $P_2$ of the cut pattern in anchor portion 1414 to provide additional longitudinal flexibility to connector portion 1416.

Figure 4:
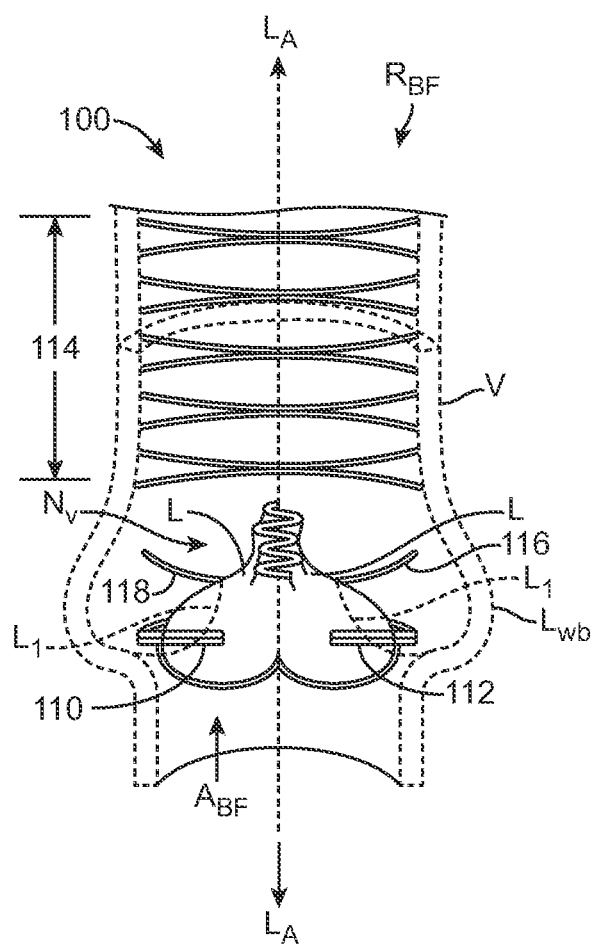
FIG. 4 depicts a sectional view of the prosthesis of FIG. 3 implanted within a vein to repair a malfunctioning valve within a vein.

FIG. 4 depicts a sectional view of prosthesis 100 of FIG. 3 implanted within a vein V to repair venous valve Nv, which had previously separated valve leaflets $L_1$ (as depicted by dashed lines in FIG. 4) due to venous wall bulge $V_{WB}$. Prosthesis 100 is shown repairing or restoring apposition between valve leaflets L of venous valve Nv by supporting valve leaflets L between valve apposition portions 110, 112. With apposition of valve leaflets L restored by prosthesis 100, retrograde blood flow $R_{BF}$ is prevented from leaking or back flowing through venous valve $N_V$. Anchor portion 114 is configured to secure a longitudinal position of prosthesis 100 within vein V and has an expanded or deployed diameter that is larger than the diameter of a healthy portion of vein V downstream of venous valve $N_V$ in the direction of antegrade blood flow $A_{BF}$. Due to the high dispensability of some veins, in accordance with embodiments hereof, the expanded or deployed diameter of the anchor portion may be made significantly larger than the diameter of a healthy portion of the vein V in which it is to be deployed to maintain fixation.

In an embodiment, spikes or other anchoring structure (not shown) may be used along anchor portion 114 to aid in securing the longitudinal position of prosthesis 100. The respective windings of connector portions 116, 118 have an expanded or deployed diameter that is substantially equal to the expanded or deployed diameter of the windings of anchor portion 114 so as to prevent interference with the function of the venous valve Nv, and particularly the valve leaflets L that are surrounded thereby. By substantially equal deployed diameters it is meant that each of the connector portions and the anchor portion are formed to have the same diameter or to have diameters that differ no more than 10%. In an embodiment, a length of prosthesis 100 is twice the diameter of the vessel in which it is implanted in order to assure self-centering and proper hold of the prosthesis within the patient's vein.

Prosthesis 100 may be delivered through the vasculature to a target site of a malfunctioning venous valve in a minimally invasive endovascular/endoluminal approach. The endovascular approach generally involves opening a vein with a needle, inserting a guidewire into the vein through the lumen of the needle, withdrawing the needle, inserting over the guidewire a dilator located inside an associated sheath introducer having a hemostasis valve, removing the dilator and inserting a delivery catheter through the hemostasis valve and sheath introducer into the blood vessel. The delivery catheter with prosthesis 100 secured therein may then be tracked through the vasculature to the target site. Alternatively, the delivery catheter with prosthesis 100 may be routed through the vasculature over a guidewire without use of an associated sheath introducer. For example, a delivery catheter loaded with prosthesis 100 can be percutaneously introduced into the vasculature, for e.g., into a greater saphenous vein, and prosthesis 100 may then be delivered endovascularly to the treatment site where it is then deployed.

Figure 5:
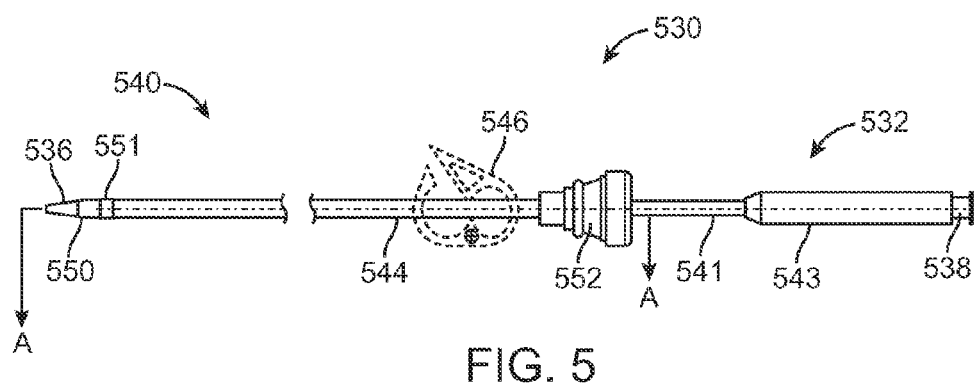
FIG. 5 is a side view of a delivery system in accordance with an embodiment hereof.
Figure 5A:
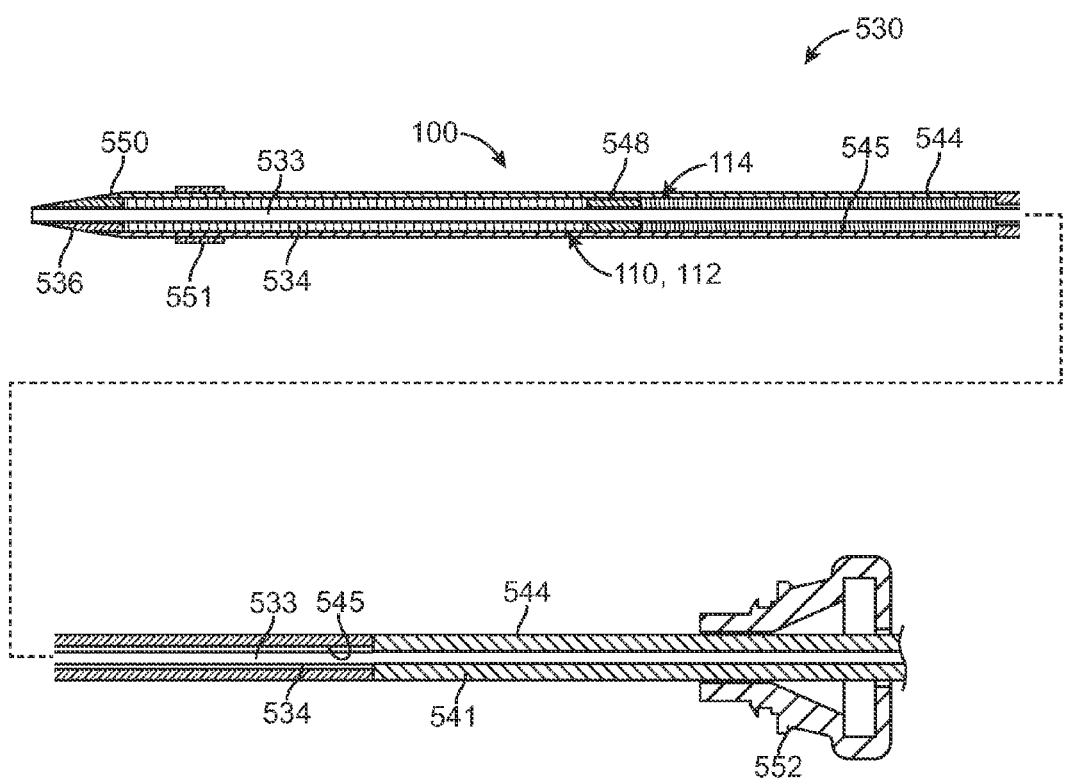
FIG. 5A is a sectional view of the delivery system of FIG. 5 taken along line A-A thereof.
Figure 6:
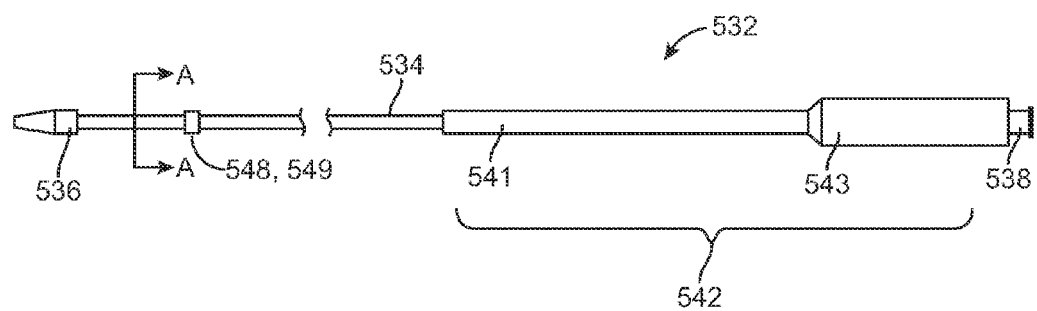
FIG. 6 is a side view of a catheter component of the delivery system shown in FIG. 5 in accordance with an embodiment hereof.
Figure 6A:
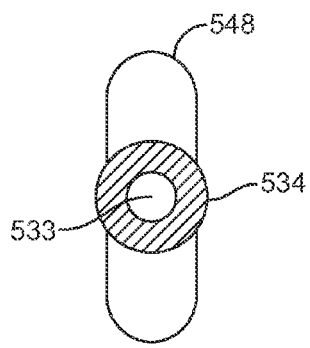
FIG. 6A is a cross-sectional view of the catheter component of FIG. 6 taken along line A-A thereof.
Figure 7:
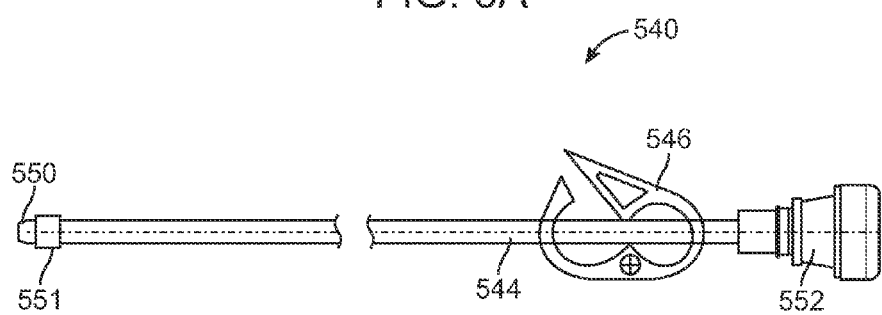
FIG. 7 is a side view of a sheath component of the delivery system shown in FIG. 5 in accordance with an embodiment hereof.
Figure 8:
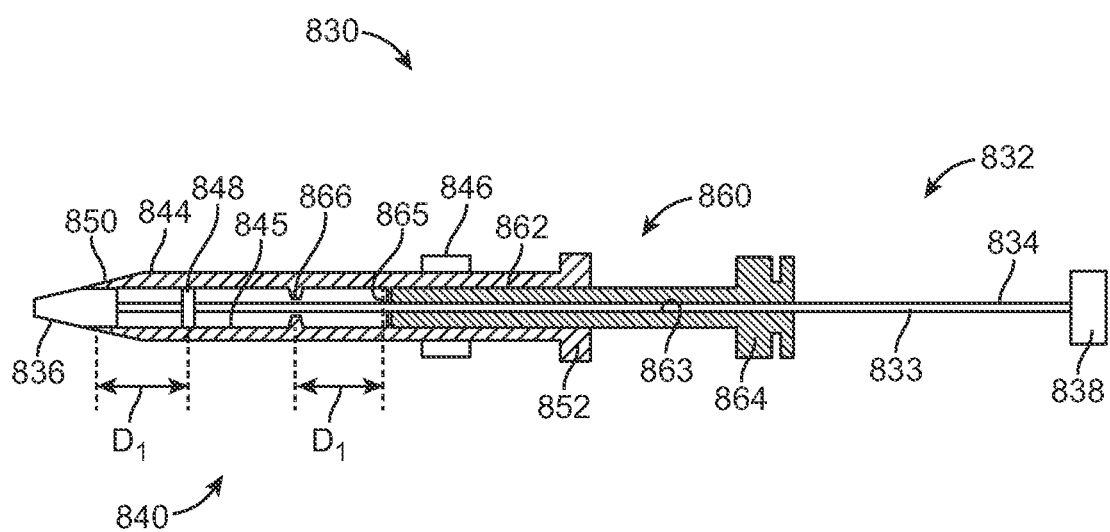
FIG. 8 is a side view of a delivery system in accordance with another embodiment hereof.

In embodiments hereof one of endovascular prosthesis delivery system 530 shown in FIGS. 5-7 and endovascular prosthesis delivery system 830 shown in FIG. 8 may be used to deliver and deploy prosthesis 100 at the treatment site for repair of a malfunctioning venous valve. With reference to FIGS. 5-7, delivery system 530 includes a catheter component 532 and a sheath component 540. Catheter component 532 includes an elongate catheter inner shaft 534 defining a guidewire lumen 533 therethrough that has an atraumatic tapered tip 536 attached to a distal end thereof and a hub 538 for accepting a guidewire attached at a proximal end thereof. Catheter component 532 also includes a handle 542 attached to the proximal end of catheter shaft 534 that has a stepped outer diameter such that handle 542 includes a smaller diameter distal section 541 for receipt within a proximal portion of sheath component 540, as described below, and a larger diameter proximal section 543 for manipulation by the clinician. A stopper 548 is attached to an outer surface of catheter shaft 534 to radially extend therefrom and is disposed proximal of distal tip 536 at a position to permit loading of anchor portion 114 of prosthesis 100 on a proximal side of stopper 548 while first and second valve apposition portions 110, 112 of prosthesis 100 are loaded on a distal side of stopper 548, as described in more detail below. In an embodiment, stopper 548 has an oval shape to extend in opposite radial directions from catheter shaft 534 as shown in FIG. 6A, which permits connector portions 116, 118 of prosthesis 100 to freely extend on either side thereof between anchor portion 114 and a respective first and second valve apposition portion 110, 112 when prosthesis 100 is loaded as noted above.

Sheath component 540 includes an elongate tubular sheath 544 defining a delivery lumen 545 therethrough that has a tapered tip 550 at a distal end thereof and a sheath handle 552 attached to a proximal end thereof for manipulation by a clinician. In an embodiment, sheath handle 552 includes a hemostasis valve (not shown) that serves as one-way valve to prevent blood loss from between catheter shaft 534 and tubular sheath 544. As shown in FIG. 5A, delivery lumen 545 of tubular sheath 544 is sized to have a sliding relationship with stopper 548 and thus is sized to receive catheter shaft 534 therein so as to hold prosthesis 100 in the delivery configuration described above. Stopper 548 functions to restrict longitudinal movement of prosthesis 100 relative to catheter shaft 534 when sheath 544 is proximally retracted during deployment of prosthesis 100, as described below. In addition, stopper 548 permits staged deployment of prosthesis 100 by allowing first and second valve apposition portions 110, 112 of prosthesis 100 to be released to return to their expanded configuration while anchor portion 114 of prosthesis 100 remains compressed within delivery system 530, to thereby facilitate during deployment the adjustment of a position of first and second valve apposition portions 110, 112 with respect to the valve leaflets of the malfunctioning venous valve.

In an embodiment, tapered tip 550 includes a marker band 551 there around to permit visualization of a position of the distal opening of tubular sheath 544 and stopper 548 includes a marker band 549 there around to permit visualization of a position of tapered tip 550 in relation to stopper 548 during deployment. In an alternate embodiment instead of stopper 548 including marker band 549, a print marker (not shown) may be made on catheter shaft 534 that represents how far tubular sheath 544 may be retracted in order to only release first and second valve apposition portions 110, 112 of prosthesis 100 therefrom.

When tubular sheath 544 is fully advanced over catheter shaft 534 as shown in FIG. 5, the tapered distal tip 536 of catheter component 532 mates with the tapered tip 550 of tubular sheath 544 to create a smooth transition for tracking delivery system 530 to the treatment site within the vasculature. In addition, smaller diameter distal section 541 of catheter handle 542 is sized to be received within delivery lumen 545 of tubular sheath 544 to permit catheter component 532 and sheath component 540 to be secured together by a clamping device 546 during introduction and tracking of delivery system 530 to the treatment site within the vasculature. Clamping device 546 is configured to temporarily lock the catheter and tubular sheath components of the delivery system together to prevent relative longitudinal movement therebetween.

In an embodiment, prosthesis 100 is loaded within a distal section of delivery system 100 by first threading prosthesis 100 over distal tip 536 of catheter component 532 so that the prosthesis partly sits distal of and partly sits proximal of stopper 548, as described above and shown in FIG. 5A. Prosthesis 100 is then compressed toward catheter shaft 534 into a reduced diameter delivery configuration and tubular sheath 544 is distally advanced there over until tapered tip 550 of sheath component 540 abuts with distal tip 536 of catheter component 532. Thereafter catheter component 532 and sheath component are fixed to one and other by securing clamping device 546.

Prosthesis 100 is intended to be implanted downstream of a malfunctioning venous valve in order to exert pressure on the valve leaflets of the venous valve. In an embodiment hereof, delivery system 530 with prosthesis 100 loaded therein as described in the preceding paragraph is introduced into the vasculature above the Saphenous Junction according to standard percutaneous entry techniques to permit advancement of delivery system 530 through the vasculature to the affected venous valve in a retrograde venous approach. Initially a guidewire may be introduced to cross the treatment site such that delivery system 530 may be tracked over the guidewire and advanced to the treatment site. Once delivery system 530 is tracked to the treatment site, clamping device 546 is opened to permit movement between catheter component 532 and sheath component 540. Sheath component 540 is then proximally retracted until tapered tip 550 is aligned with stopper 548, such that first and second valve apposition portions 110, 112 of prosthesis 100 are released to return to their expanded configurations downstream of the malfunctioning venous valve. Clamping device 546 is then used to secure catheter component 532 and sheath component 540 together to fix the new position of tubular sheath 544 relative to catheter shaft 534. Thereafter rotation and advancement of delivery system 530 permits first and second valve apposition portions 110, 112 of prosthesis 100 to be properly aligned with the valve leaflets so that delivery system 530 may then be distally advanced until the valve leaflets are positioned between and contacted by first and second valve apposition portions 110, 112. In an embodiment, correct positioning of the first and second valve apposition portions 110, 112 would be verified with the use of fluoroscopy and/or ultrasound at this stage of the procedure. Clamping device 546 is opened again so that sheath component 540 may be proximally retracted a sufficient distance to permit anchor portion 114 to return to its expanded configuration and thereby fully release or deploy prosthesis 100 from the delivery system. Delivery system 530 is then removed from the vasculature.

With reference to FIG. 8, delivery system 830 includes a catheter component 832, a sheath component 840 and a tubular stopper component 860. Catheter component 832 includes an elongate catheter shaft 834 defining a guidewire lumen 833 therethrough that has a tapered tip 836 attached to a distal end thereof and a hub 838 for accepting a guidewire attached at a proximal end thereof. A stopper 848 is attached to an outer surface of catheter shaft 834 to radially extend therefrom and is disposed proximal of distal tip 836 at a position to permit loading of anchor portion 114 of prosthesis 100 on a proximal side of stopper 848 while first and second valve apposition portions 110, 112 of prosthesis 100 are loaded on a distal side of stopper 848 to function as similarly described with reference to stopper 548 of delivery system 530.

Tubular stopper component 860 includes an elongate tubular stopper shaft 862 that defines a lumen 863 through which catheter component 832 extends. A handle 864 is attached to a proximal end of stopper shaft 862 for manipulation by a clinician. In an embodiment, handle 864 includes a hemostasis valve (not shown) that serves as a one-way valve to prevent blood loss between catheter shaft 834 and stopper shaft 862 and/or includes a locking mechanism (not shown) with which stopper component 860 may be fastened to catheter shaft 834 by screwing.

Sheath component 840 includes an elongate tubular sheath 844 defining a delivery lumen 845 therethrough that has a tapered tip 850 at a distal end thereof and a sheath handle 852 attached to a proximal end thereof for manipulation by a clinician. In an embodiment, sheath handle 852 includes a hemostasis valve (not shown) that serves as a one-way valve which prevents blood loss between tubular sheath 844 and stopper shaft 862. Tubular sheath 844 includes an internal ridge 866 that protrudes into delivery lumen 845 distal of stopper shaft 862. Other than at ridge 866, delivery lumen 845 is sized to have a sliding relationship with stopper 848 and stopper shaft 862.

As similarly described with reference to delivery system 530, prosthesis 100 is held in a radially compressed delivery configuration within a distal section of delivery system 830 between tubular sheath 844 and catheter shaft 834 with stopper 848 being positioned between first and second valve apposition portions 110, 112 and anchor portion 114 as described above. Stopper 848 functions to restrict longitudinal movement of prosthesis 100 relative to catheter shaft 834 when sheath 844 is proximally retracted during deployment of prosthesis 100, as described below.

Stopper component 860 is slidable relative to each of catheter component 832 and sheath component 840. Stopper component 860 is configured to be selectively fixed and positioned with respect to catheter component 832 via the locking mechanism of stopper handle 864 to permit proximal retraction of sheath 844 until ridge 866 of sheath 844 contacts a distal end 865 of stopper shaft 862. For example, in FIG. 8 delivery system 830 is shown secured by clamping device 846 in a first delivery configuration that permits the staged release of prosthesis 100. In the first delivery configuration, stopper component 860 is fixed to catheter component 832 such that distal end 865 of stopper shaft 862 is proximally spaced from ridge 866 a distance $D_1$, which is the same distance $D_1$ between distal tip 850 of tubular sheath 844 and stopper 848. Accordingly, after delivery system 830 has been introduced and tracked through the vasculature to a treatment site and clamping device 846 has been released, as similarly described with reference to delivery system 532, tubular sheath 844 may be proximally retracted the distance $D_1$ until ridge 866 abuts distal end 865 of stopper shaft 862, which corresponds to distal tip 850 of sheath 844 being retracted and positioned at or over stopper 848. In such a partially deployed configuration, first and second valve apposition portions 110, 112 of prosthesis 100 are released to return to their expanded configurations. Clamping device 846 is then used to secure delivery system 830 in the new position, which may be considered a second delivery configuration with tubular sheath 844 retracted to stopper 848. Thereafter, first and second valve apposition portions 110, 112 may be maneuvered to align with the venous valve leaflets, wherein once alignment is confirmed then delivery system 830 may be distally advanced until the valve leaflets are positioned between and contacted by first and second valve apposition portions 110, 112. In order to deploy anchor portion 114 of prosthesis 100, stopper handle 864 is unlocked from catheter shaft 834 so that stopper component 860 may be proximally withdrawn a sufficient distance, such as approximately 2 to 5 cm, to release anchor portion 114 from tubular sheath 844 so that anchor portion 114 returns to its expanded configuration. Delivery system 830 is then removed from the vasculature.

In accordance with embodiments hereof, catheter shafts 532, 832, tubular sheaths 544, 844 and stopper shaft 862 are generally thin-walled, flexible tubular structures of a polymeric material, such as polyether block amide copolymer, polyvinyl chloride, polyethylene, polyethylene terephthalate, polyamide, or polyimide, and may be formed from one or more tubular components. Optionally, catheter shafts 532, 832, tubular sheaths 544, 844 and stopper shaft 862 or some portion thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like of a suitable biocompatible metal or metal alloy.

In an embodiment, distal sections of tubular sheaths 544, 844 that cover and compress prosthesis 100 may be composite tubular structures of a polymeric material that is reinforced with a braided or webbed layer of a suitable biocompatible metal or metal alloy. In embodiments hereof, distal tips 536, 836 are soft atraumatic structures that may be formed from a suitable polymer, such as polyether block amide, polyurethane, or silicone elastomer. In embodiments hereof, hubs 538, 838 and handles 552, 852, 864 are molded polymeric structures of polycarbonate, acetal or polyamide or similar injection molded polymer that may include fittings, one-way valves and/or locking mechanisms as would be understood by one of ordinary skill in the art. Components may be joined using a number of techniques including heat bonding using hot air or lasers or adhesives, such as cyanoacrolate.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An endovascular prosthesis for restoring apposition to valve leaflets of a native valve comprising:
   a wire forming a first helix from a distal end to a proximal end of the prosthesis and forming a second helix wound on top of and concentric with the first helix from the proximal end to the distal end of the prosthesis to define a tubular body having a blood flow lumen therethrough, wherein first and second free ends of the wire at the distal end of the prosthesis define respective first and second valve apposition portions that are configured to inwardly extend toward each other from opposing sides of the distal end of the prosthesis relative to a longitudinal axis of the prosthesis and to be spaced apart from each other a distance for receiving the native valve there between when the prosthesis is in a deployed configuration, and
   wherein each of the first and second valve apposition portions is a closed loop formed by the respective first or second free end of the wire and wherein the closed loops define substantially parallel valve contacting segments that are configured to contact the native valve when the prosthesis is in the deployed configuration.

2. The prosthesis of claim 1, wherein distal lengths of the first and second helix form respective first and second connector portions of the prosthesis and proximal lengths of the first and second helix form an anchor portion of the prosthesis.

3. The prosthesis of claim 2, wherein a pitch between windings of the distal lengths of the first and second helix that form the first and second connector portions is greater than a pitch between windings of proximal lengths of the first and second helix that form the anchor portion.

4. The prosthesis of claim 3, wherein each of the first and second valve apposition portions is longitudinally displaced from the anchor portion by one of the first and second connector portions to transversely extend from a respective distal end thereof.

5. The prosthesis of claim 1, wherein the prosthesis is self-expanding to return to the deployed configuration from a reduced-diameter delivery configuration.

6. The prosthesis of claim 1, wherein windings of the second helix overlay windings of the first helix.

7. An endovascular prosthesis for restoring apposition to valve leaflets of a native valve comprising:
   a tubular body defining a blood flow lumen along a longitudinal axis of the prosthesis from a proximal end to a distal end of the prosthesis, the tubular body comprising,
       an anchor portion for securing a longitudinal position of the prosthesis within a vessel,
       first and second connector portions extending from the anchor portion, and
       first and second valve apposition portions being longitudinally separated from the anchor portion by respective first and second connector portions, the first and second valve apposition portions being disposed at opposing locations at the distal end of the prosthesis and being configured to inwardly extend toward each other and to be spaced apart a distance for receiving the native valve therebetween when the prosthesis is in a deployed configuration,
   wherein the anchor portion, the first and second connector portions and the first and second valve apposition portions of the tubular body are formed from a wire that defines a first helix from the distal end to the proximal end of the prosthesis and defines a second helix wound on top of and concentric with the first helix from the proximal end to the distal end of the prosthesis, and
   wherein a deployed diameter of proximal portions of the first and second helix that form the anchor portion is substantially equal to a deployed diameter of each of the distal portions of the first and second helix that form the respective first and second connector portions.

8. The prosthesis of claim 7, wherein when the prosthesis is in the deployed configuration the native valve is held between the first and second valve apposition portions at the distal end of the prosthesis and the valve leaflets of the native valve are received within a segment of the blood flow lumen that is defined within the first and second connector portions.

9. The prosthesis of claim 7, wherein windings of the second helix overlay windings of the first helix.

10. The prosthesis of claim 7, wherein windings of the second helix are interlaid with windings of the first helix with windings of the second helix alternately crossing over and then under windings of the first helix.

11. The prosthesis of claim 7, wherein a pitch between windings of the distal portions of the first and second helix that form the first and second connector portions of the prosthesis is greater than a pitch between windings of the proximal portions of the first and second helix that form the anchor portion of the prosthesis.

\* \* \* \* \*